United States Patent
Wieters et al.

(10) Patent No.: US 11,937,775 B2
(45) Date of Patent: Mar. 26, 2024

(54) OPTICAL SYSTEM FOR AN ENDOSCOPE AND METHOD FOR FIXING A DISTAL OPTICAL ASSEMBLY TO A PROXIMAL OPTICAL ASSEMBLY OF AN OPTICAL SYSTEM FOR AN ENDOSCOPE

(71) Applicant: OLYMPUS WINTER & IBE GMBH, Hamburg (DE)

(72) Inventors: Martin Wieters, Barsbuettel (DE); Uwe Schoeler, Hoisdorf (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 864 days.

(21) Appl. No.: 17/019,563

(22) Filed: Sep. 14, 2020

(65) Prior Publication Data
US 2020/0405127 A1  Dec. 31, 2020

Related U.S. Application Data

(63) Continuation of application No. PCT/EP2019/055406, filed on Mar. 5, 2019.

(30) Foreign Application Priority Data

Mar. 14, 2018 (DE) .......................... 102018105846.2

(51) Int. Cl.
*A61B 1/00* (2006.01)
*G02B 23/24* (2006.01)

(52) U.S. Cl.
CPC ........ *A61B 1/00096* (2013.01); *A61B 1/0011* (2013.01); *A61B 1/00126* (2013.01); *G02B 23/2423* (2013.01); *G02B 23/2453* (2013.01); *G02B 23/2476* (2013.01); *G02B 23/2415* (2013.01)

(58) Field of Classification Search
USPC .......................................................... 600/175
See application file for complete search history.

(56) References Cited

U.S. PATENT DOCUMENTS

| | | | |
|---|---|---|---|
| 4,947,245 A * | 8/1990 | Ogawa | A61B 1/0607 348/66 |
| 5,411,500 A * | 5/1995 | Lafferty | A61B 1/042 606/14 |
| 5,689,365 A | 11/1997 | Takahashi | |
| 5,860,912 A | 1/1999 | Chiba | |

(Continued)

FOREIGN PATENT DOCUMENTS

| | | |
|---|---|---|
| DE | 19941320 A1 | 3/2000 |
| DE | 102004009383 A1 | 9/2005 |

(Continued)

OTHER PUBLICATIONS

International Search Report dated Jul. 18, 2019 issued in PCT/EP2019/055406.

*Primary Examiner* — John P Leubecker

(74) *Attorney, Agent, or Firm* — Scully, Scott, Murphy & Presser, P.C.

(57) ABSTRACT

An optical system for an endoscope, the optical system including: a distal optical assembly; a proximal optical assembly; and at least one elongated bar-shaped fixing element; wherein the proximal optical assembly is fastened to the distal optical assembly by the fixing element.

18 Claims, 3 Drawing Sheets

(56) References Cited

U.S. PATENT DOCUMENTS

| | | | |
|---|---|---|---|
| 6,066,102 A * | 5/2000 | Townsend | A61B 10/06 606/174 |
| 6,142,932 A * | 11/2000 | Morizumi | A61B 1/00096 600/176 |
| 6,741,778 B1 * | 5/2004 | Chan | G02B 6/4236 385/94 |
| 6,767,322 B1 | 7/2004 | Futatsugi et al. | |
| 7,691,056 B2 * | 4/2010 | Hirata | A61B 1/06 600/117 |
| 7,871,373 B2 * | 1/2011 | Yamada | A61B 1/063 600/177 |
| 8,197,398 B2 | 6/2012 | Scholly et al. | |
| 8,269,828 B2 * | 9/2012 | Miller | A61B 1/00087 348/80 |
| 2002/0099267 A1 * | 7/2002 | Wendlandt | A61B 1/05 600/173 |
| 2004/0005124 A1 * | 1/2004 | Gallup | G02B 6/4226 385/88 |
| 2004/0143162 A1 | 7/2004 | Krattiger et al. | |
| 2005/0089286 A1 * | 4/2005 | Hatori | A61B 1/0011 385/117 |
| 2005/0192477 A1 | 9/2005 | Forster et al. | |
| 2006/0058581 A1 | 3/2006 | Hanke | |
| 2007/0139953 A1 * | 6/2007 | Krattiger | A61B 1/00174 362/574 |
| 2007/0142711 A1 * | 6/2007 | Bayer | A61B 1/00101 600/172 |
| 2018/0011308 A1 | 1/2018 | Zhao | |
| 2019/0045096 A1 * | 2/2019 | Mullenary | H04N 23/57 |
| 2019/0206281 A1 * | 7/2019 | Dantes | A61B 1/051 |
| 2019/0384007 A1 * | 12/2019 | Matiss | G02B 6/1225 |

FOREIGN PATENT DOCUMENTS

| | | |
|---|---|---|
| DE | 102007032202 A1 | 1/2009 |
| DE | 102010040166 A1 | 3/2012 |
| DE | 102016212470 A1 | 1/2018 |
| JP | H 08-29701 A | 2/1996 |
| JP | 2000-010022 A | 1/2000 |
| JP | 2000-342512 A | 12/2000 |
| JP | 2009-018164 A | 1/2009 |
| WO | WO 02/087426 A2 | 11/2002 |
| WO | WO 2009/054860 A1 | 4/2009 |

* cited by examiner

OPTICAL SYSTEM FOR AN ENDOSCOPE AND METHOD FOR FIXING A DISTAL OPTICAL ASSEMBLY TO A PROXIMAL OPTICAL ASSEMBLY OF AN OPTICAL SYSTEM FOR AN ENDOSCOPE

CROSS-REFERENCE TO RELATED APPLICATION

The present application is a continuation of PCT/EP2019/055406 filed on Mar. 5, 2019, which is based upon and claims the benefit to DE 10 2018 105 846.2 filed on Mar. 14, 2018, the entire contents of each of which are incorporated herein by reference.

BACKGROUND

Field

The present disclosure relates to an optical system for an endoscope, comprising a distal optical assembly and a proximal optical assembly. Furthermore, the present disclosure relates to an endoscope and a method for fixing a proximal optical assembly to a distal optical assembly of an optical system for an endoscope.

Prior Art

With medical endoscopes, a small outside diameter of the endoscope shaft is desirable. Due to increasing miniaturization, the production and assembly of the optical system constitute a technical challenge. Thus, it has to be guaranteed, for example, during the miniaturization of the optical system that the optical properties of the endoscope comply with the specifications and the endoscope simultaneously withstands the stresses to which it is exposed during operation and during preparation. This also applies especially to the holders in the optical system, which receive components such as, for example, optical elements and image sensors.

Stereo-video endoscopes have two lens system channels which are separated from one another and which, in each case, image light bundles from a field of view having a slightly different viewing angle in each case on an image sensor. In this way, a stereo image of the receiving region can be composed, which provides an observer with a spatial impression. The use of two lens system channels requires a particularly space-saving design of the optical system, so as not to unnecessarily enlarge the outside diameter of the stereo-video endoscope.

SUMMARY

It is an object to indicate a holder for an optical system of an endoscope, an optical system for an endoscope, an endoscope and a method for producing a holder for an optical system of an endoscope, wherein the holder is intended to make possible a stable and reliable construction with a small installation space.

Such object can be solved by an optical system for an endoscope, comprising a distal optical assembly and a proximal optical assembly, wherein the optical system has at least one bar-shaped fixing element having an elongate form, and the proximal optical assembly is fastened to the distal optical assembly by the fixing element.

The fixing element can extend in a direction parallel to a longitudinal axis of the optical system. Thanks to the alignment of the fixing element in a direction parallel to the longitudinal axis of the optical system, the alignment of the proximal optical assembly in relation to the distal optical assembly is simplified. An alignment diagonally to the longitudinal axis of the optical system can also be provided.

In the context of the present specification, a distal optical assembly denotes an optical assembly which lies distally of the proximal optical assembly which is likewise mentioned. The same applies to the proximal optical assembly.

The distal optical assembly can comprise an inlet lens. The proximal optical assembly can comprise at least one image sensor.

A space-saving fixing can be achieved by a fixing element having an elongate form. An elongate form of the fixing element denotes a fixing element which has, for example, the form of an oblong pin or bar. In any case, the fixing element can be oblong, i.e. it has a longitudinal extension direction, in which its dimension is larger or substantially larger than in a direction perpendicular to said longitudinal extension direction. For example, a length of the fixing element can be at least twice as large as its diameter.

Other than in the case of variants for fixing, in which one of the assemblies encloses the other assembly annularly, an enlargement of the enclosing assembly in the radial direction can be superfluous in the case of a fixing with one or more fixing element(s).

The fixing element can have a cylindrical form, wherein a cylinder axis of the fixing element extends parallel to the longitudinal axis of the optical system. A cylindrical fixing element is, on the one hand, easy to produce; on the other hand, the lateral surfaces and top surfaces of a cylinder are very suitable as contact surfaces for a fixing.

The fixing element can be bar-shaped. Thus, the fixing element can be a solid cylinder where no optical elements are arranged in its interior. The fixing element can have a circular cross-section.

The fixing element can be a rigid, non-flexible or non-bendable body. The fixing element can be free of hollow spaces. The rigid, hollow space-free embodiment of the fixing element provides a stable configuration.

The space taken up by the fixing element can lie completely outside of the beam path of the incident light into the optical system.

The fixing element can connect a mount of the distal optical assembly, in which at least one optical element is received, to a holder of the proximal optical assembly, in which at least one further optical element and/or an image sensor is/are received.

The fixing element can project in the proximal direction from a front side of the mount of the distal optical assembly. The front side of the mount terminates the distal optical assembly in the proximal direction. A diameter of the fixing element can be smaller than a diameter of the mount. Furthermore, the diameter of the fixing element can be smaller than a diameter of the at least one optical element received in the mount.

According to an embodiment, the fixing element can be formed integrally with the distal optical assembly. In this embodiment, the fixing element can be configured as part of the mount of the distal optical assembly such that it is manufactured integrally, together with the mount, as part of the mount.

According to an alternative embodiment, the fixing element can be formed as a separate element and fixed, such as by welding, in a mount of the distal optical assembly. In this embodiment, the distal optical assembly and the fixing element are formed separately. Thus, both the manufacture of the distal optical assembly or of the mount of the distal optical assembly and the production of the fixing element can be simplified. A stable fixing is achieved by welding the fixing element into the mount of the distal assembly, however, other forms of fixing the fixing element are also contemplated, such as soldering and bonding.

The fixing element can be formed from a base material and provided with a coating, wherein the coating can have better solderability than the base material.

Furthermore, the fixing element can be formed from a base material and the mount of the distal optical assembly can be manufactured from a mount material, wherein the base material differs from the mount material.

The selection of the mount material may be restricted by the striven-for properties of the distal optical assembly. However, it is possible, where the fixing element is formed as a separate element, to select another material than the mount material as the base material of the fixing element. As a result of the selection of the base material, the thermal conductivity and/or the thermal expansion coefficient of the fixing element can, for example, be adapted. A material which is very suitable for the fixing to the distal optical assembly and/or the proximal optical assembly can be selected as the coating of the fixing element.

The fixing element can be fixed to the proximal optical assembly by means of a soldered connection. Laser soldering can be deployed as the soldering method. Consequently, a material having good solderability such as, for example, gold, silver or tin can be selected as the coating of the fixing element.

According to a further embodiment, the proximal optical assembly comprises a first holder and a second holder which are each designed to receive an image sensor, wherein the first holder can be axisymmetrical with respect to the second holder in relation to the longitudinal axis of the optical system, wherein the first holder and the second holder can be fixed to one another.

An optical system according to this embodiment may be suitable for a stereo-video endoscope. In this embodiment, the proximal optical assembly comprises the two holders and the components arranged on the holders. Due to the symmetrical arrangement, a space-saving design of the proximal optical assembly can be achieved. The stability of the proximal optical assembly can be increased by fixing the first holder and the second holder to one another.

A circumferential circle can be used around both holders together, substantially similar to a circumferential circle around the mount of the distal optical assembly, in the radial direction. The radial direction is perpendicular to the longitudinal axis of the optical system, so that the area of the circumferential circles is perpendicular to the longitudinal axis. Thus, the outside diameter of the distal optical assembly substantially corresponds to the outside diameter of the distal optical assembly. A space-saving construction of the optical system can be achieved in this way.

In a further embodiment, the optical system can comprise a first fixing element and a second fixing element, wherein the first fixing element fixes the first holder and the second fixing element fixes the second holder to the distal optical assembly. A fixing element can be provided for each holder, with which fixing element said holder is fixed to the distal optical assembly.

According to an alternative embodiment, the optical system can comprises a first fixing element and a second fixing element, wherein each holder has in each case a first fixing region and a second fixing region, wherein the first fixing element fixes the distal optical assembly to the first fixing region of the second holder and to the second fixing region of the first holder, wherein the second fixing element fixes the distal optical assembly to the first fixing region of the first holder and to the second fixing region of the second holder. In this embodiment, each holder can comprise two fixing regions which are, in each case, fastened to one of the two fixing elements. In other words, each of the two holders can be fastened to each of the two fixing elements. Such configuration "crisscross" fastening to provide a stable construction, i.e. a stable fixing of the holders and the proximal optical assembly to the distal optical assembly.

The optical system can comprise a first lens system channel having a first optical axis and a second lens system channel having a second optical axis, wherein the first optical axis runs parallel to the second optical axis and to the longitudinal axis of the optical system, wherein a first fixing element is arranged above the first lens system channel and a second fixing element is arranged below the second lens system channel. The terms above and below are based on a plane which is spanned by the optical axes. Due to such configuration of the fixing elements, the stability of the fixing of the proximal optical assembly or holders fastened to the fixing elements can be increased. Two holders can be fastened in a crisscross manner to the fixing elements so that each holder is fixed to both fixing elements.

Thus, the optical system can be an optical system of a stereo-video endoscope. The terms "distal optical assembly" and "proximal optical assembly" are understood, in the context of the present description and in the context of a stereo-video endoscope, to mean that both the distal and the proximal optical assembly are a part of an assembly in which the two optical channels (left channel and right channel) are guided separately.

Such object is, in addition, can be solved by an endoscope, such as a stereo-video endoscope, comprising an optical system according to one of the previously described embodiments.

The endoscope also has the same or similar advantages to those with respect to the optical system.

Furthermore, such object can be solved by a method for fixing a proximal optical assembly to a distal optical assembly of an optical system for an endoscope, wherein the proximal optical assembly is fixed to the distal optical assembly by means of a bar-shaped fixing element, and the fixing element has an elongate form.

The elongate form of the fixing element can extend, following fixing, in a direction parallel to a longitudinal axis of the optical system.

According to an embodiment, the fixing element can be formed integrally with the distal optical assembly. In an alternative embodiment, the fixing element can be formed as a separate element, wherein the fixing element is fixed, such as by welding, in a mount of the distal optical assembly. In this embodiment, the fixing element can be formed from a base material and can be, subsequently, coated with a covering material, wherein the covering material has better solderability than the base material.

Furthermore, the fixing element can be fixed to the proximal optical assembly by means of a soldered connection.

The same or similar advantages, features and properties with respect to the optical system also apply to the method for fixing a proximal optical assembly to a distal optical assembly.

BRIEF DESCRIPTION OF THE DRAWINGS

Further features will become evident from the description of embodiments, together with the claims and the appended drawings. Embodiments can fulfill individual features or a combination of multiple features.

The embodiments will be described below without limiting the general concept of the invention by means of exemplary embodiments with reference to the drawings, wherein reference is expressly made to the drawings regarding all of the details which are not explained in greater detail in the text, wherein.

In the drawings, the same or similar elements and/or parts are, in each case, provided with the same reference numerals so that they are not introduced again in each case.

DETAILED DESCRIPTION

Figure 1:
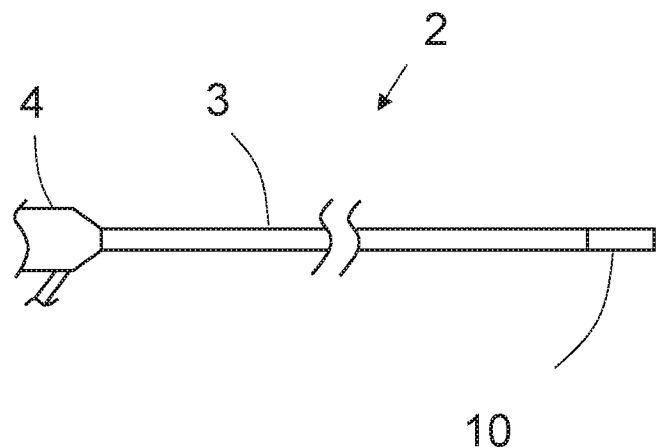
FIG. 1 illustrates a schematically simplified representation of a section of an endoscope.

FIG. 1 shows a schematically simplified representation of a section of an endoscope 2 having a shaft 3 and a handle 4. The endoscope 2 is, for example, a video endoscope, additionally for example a stereo-video endoscope. An optical system 10 is situated at a distal end of the shaft 3.

Figure 2:
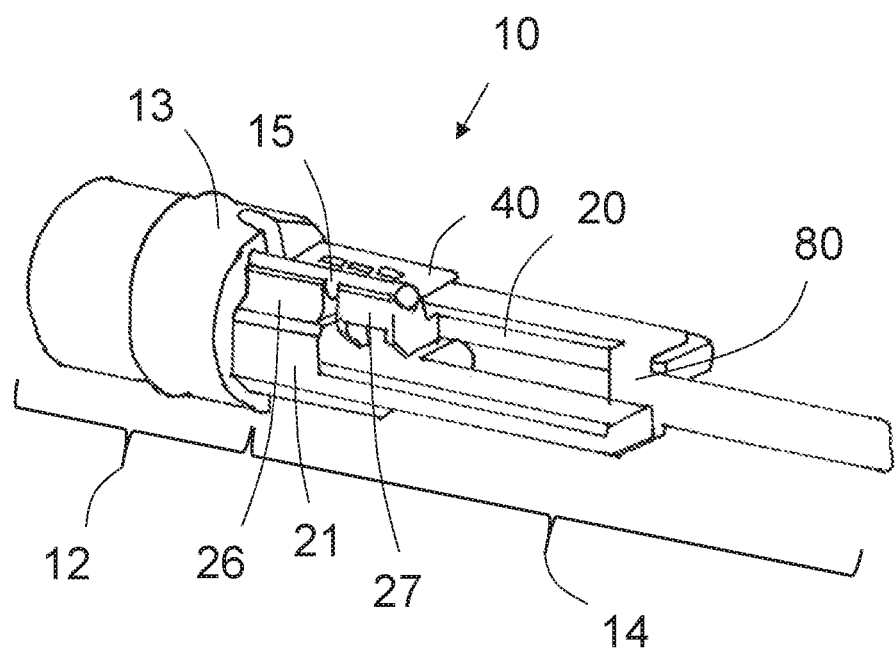
FIG. 2 illustrates a schematically simplified perspective representation of an optical system for a stereo-video endoscope having two holders.

An optical system 10 for a stereo-video endoscope is shown schematically in a simplified manner in FIG. 2. The optical system 10 comprises a distal optical assembly 12 and a proximal optical assembly 14. The optical system 10, that is to say the distal optical assembly 12 and the proximal optical assembly 14, is situated in a part or portion of the entire optical system of the stereo-video endoscope, in which the two optical channels (left channel and right channel) are guided separately.

A number of optical elements, which are not depicted in FIG. 2, are arranged in the distal optical assembly 12. Light bundles incident from a treatment and/or observation space at a distal tip of the shaft 3 are received by the distal optical assembly 12 and forwarded to the proximal optical assembly 14. The proximal optical assembly 14 comprises two image sensors 40, merely one of which is visible in FIG. 2. The image sensors 40 are coupled to (for example, flexible) printed circuit boards 80 for forwarding image signals in the direction of the handle 4, for example mounted on the relevant printed circuit boards 80.

The embodiment of the optical system 10, which is shown in FIG. 2, comprises a proximal optical assembly 14 having a first holder 20 and a second holder 21 which are configured to receive the image sensors 40. In order to fix the proximal optical assembly 14 to the distal optical assembly 12, the first holder 20 and the second holder 21 each have a first fixing region 26 and a second fixing region 27. The fixing regions 26, 27 are configured to receive a cylindrical fixing element 15.

In the display selected for FIG. 2, merely the first fixing region 26 of the second holder 21 and the second fixing region 27 of the first holder 20, which are soldered to a first fixing element 15, are visible. The second fixing element 16 is hidden in FIG. 2. The fixing elements 15, 16 are fastened to the distal optical assembly 12 and are, in each case, fixed to the first fixing region 26 of a holder 20, 21 and to the second fixing region 27 of the other holder 20, 21 with a soldered connection. The fixing elements 15, 16 extend, for example, in a direction parallel to a longitudinal axis 56 of the optical system 10. An alignment diagonally to the longitudinal axis 56 of the optical system 10 can also be provided. In this way, a very stable and space-saving arrangement of the holders 20, 21 is achieved.

Figure 3:
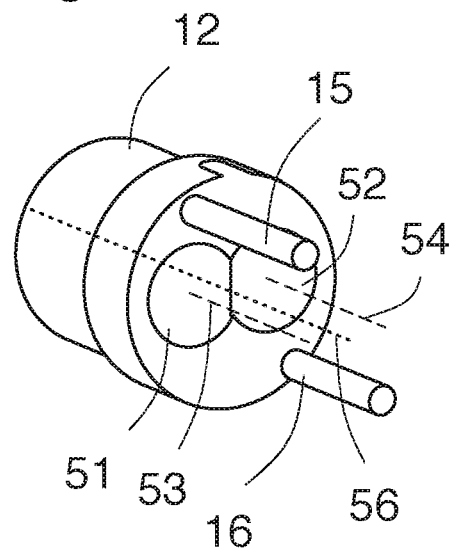
FIG. 3 illustrates a schematically simplified perspective representation of a distal assembly of an optical system for a stereo-video endoscope having two fixing elements.

FIG. 3 shows a schematically simplified representation of the distal optical assembly 12, in which the two fixing elements 15, 16 can be seen. In addition, a first lens system channel 51 having a first optical axis 53 and a second lens system channel 52 having a second optical axis 54 are depicted. A longitudinal axis 56 of the optical assembly 12 extends centrally between the two optical axes 53, 54. The first fixing element 15 is arranged above and the second fixing element 16 is arranged below the lens system channels 51, 52.

Figure 4:
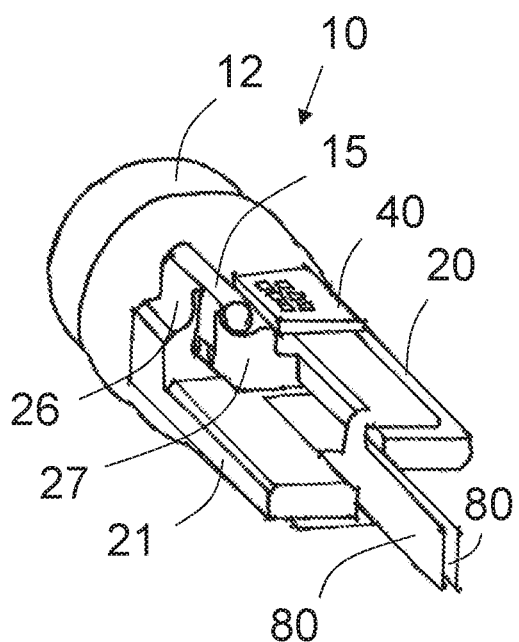
FIG. 4 illustrates a schematically simplified perspective representation of an optical system for a stereo-video endoscope having two holders in a rotated view.

A further schematically simplified perspective representation of the optical system 10 is shown in FIG. 4. It can be seen in this representation that a printed circuit board 80 is in each case connected to an image sensor 40. Since the image sensors 40 are arranged parallel to the longitudinal axis 56, deflection prisms are arranged in the holders 20, 21, which are hidden in FIGS. 2 to 4. The deflection prisms deflect the light bundles incident along the optical axes 53, 54 in the direction of the image sensors 40.

Figure 5:
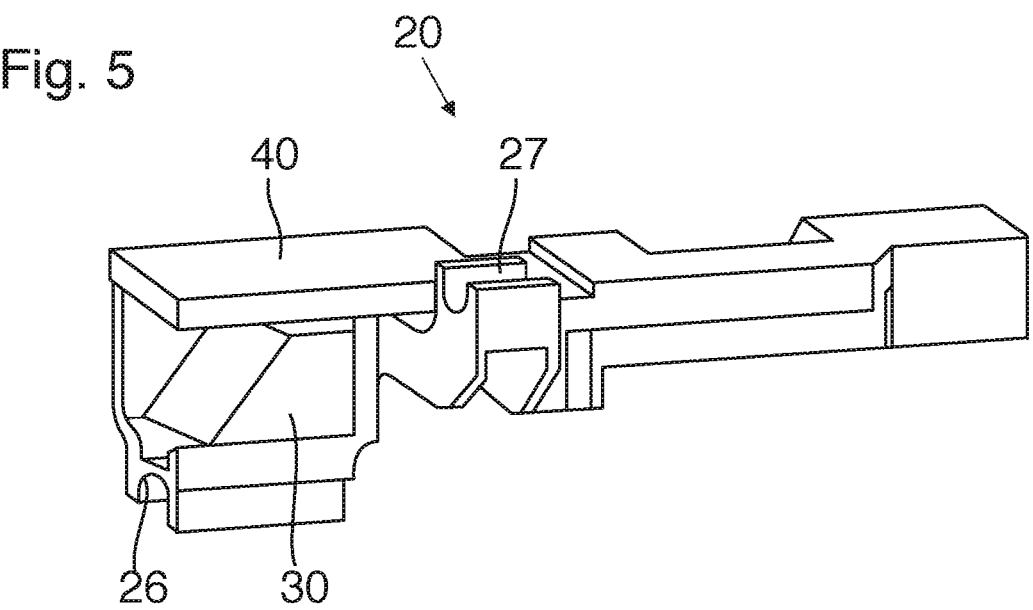
FIG. 5 illustrates a schematically simplified perspective representation of a holder for an optical system of an endoscope.

FIG. 5 shows a schematic representation of a holder 20. The arrangement of the first fixing region 26, of the second fixing region 27 and of the image sensor 40 can be seen. In addition, an optical element 30 in the form of a deflection prism which deflects incident light bundles in the direction of the image sensor 40 is shown.

Figure 6A:
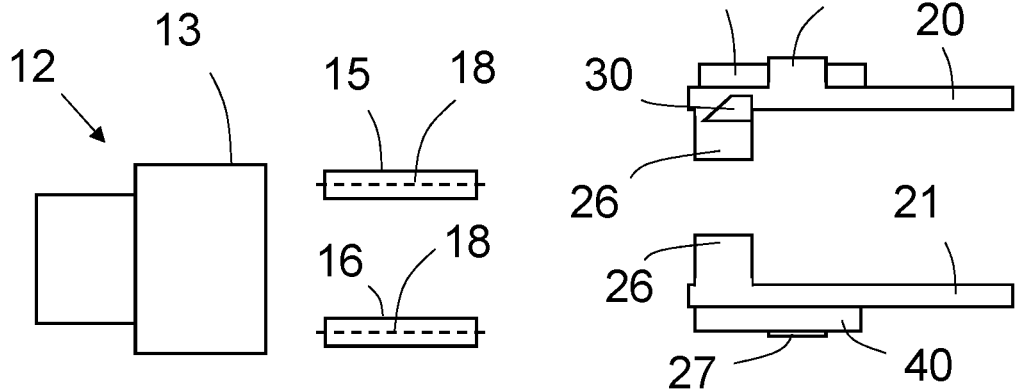
FIGS. 6A to 6D illustrate a schematically simplified representation of a method for fixing a proximal optical assembly to a distal optical assembly.
Figure 6B:
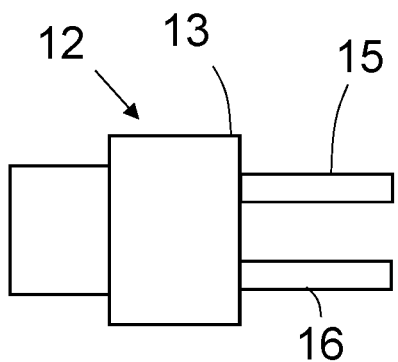
Figure 6C:
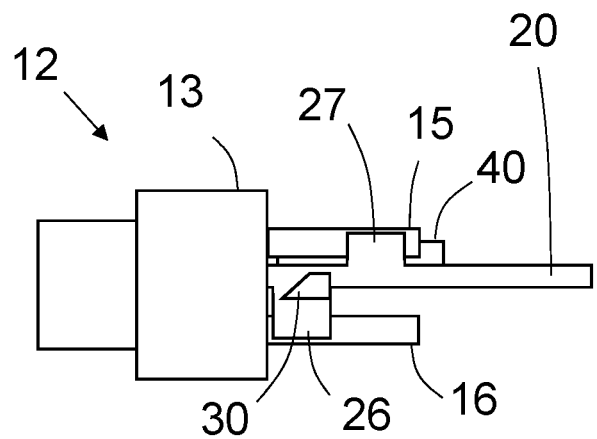

FIGS. 6A to 6D schematically show a method for fixing a proximal optical assembly to a distal optical assembly using the example of the optical system 10 which is depicted in FIGS. 2 to 4, which optical system is depicted in a simplified lateral view in FIGS. 6A to 6C.

FIG. 6A shows the components which are manufactured prior to the performance of the method. The distal optical assembly 12 having the mount 13 is shown. An objective is, for example, arranged in the mount 13. In addition, the fixing elements 15, 16 are manufactured from a base material and, if necessary, provided with a coating, wherein the coating has better solderability than the base material. The fixing elements 15, 16 have a cylindrical form having a cylinder axis 18. The holders 20, 21 are also provided, wherein an image sensor 40 and an optical element 30, in this case a deflection prism, are in each case received in the holders 20, 21. In the case of the holder 21, the optical element 30 is hidden because of the viewing angle.

As shown in FIG. 6B, the fixing elements 15, 16 are fixed to the mount 13 initially, for example by welding, soldering or bonding the fixing elements 15, 16 into cavities of the mount 13.

The first holder 20 is subsequently fastened to the fixing elements 15, 16, as shown in FIG. 6C. To this end, the alignment of the first holder 20 is first tweaked. For example, the optical path length from the objective in the mount 13 via the optical element 30 to the image sensor 40 arranged on the first holder 20 is adjusted. The first fixing region 26 of the first holder 20 is subsequently fixed to the second fixing element 16, and the second fixing region 27 of the first holder 20 is subsequently fixed to the first fixing element 15 by means of a soldered connection.

Figure 6D:
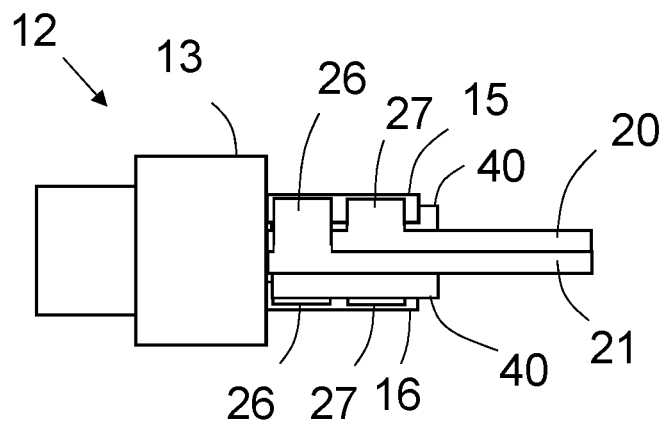

Lastly, the second holder is fastened to the fixing elements 15, 16, as shown in FIG. 6D. In the process, as in the case of the first holder 20, the alignment of the second holder 21 is tweaked first and the first fixing region 26 of the second holder 21 is subsequently fixed to the first fixing element 15, and the second fixing region 27 of the second holder 21 is fixed to the second fixing element 16 by means of a soldered connection. Thanks to the crossed arrangement of the fixing regions 26, 27 of each of the holders 20, 21, a high stability and large torsional stiffness are achieved.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Endoscope
3 Shaft
4 Handle
10 Optical system
12 Distal optical assembly
13 Mount
14 Proximal optical assembly
15 First fixing element
16 Second fixing element
18 Cylinder axis
20 First holder
21 Second holder
26 First fixing region
27 Second fixing region
30 Optical element
40 Image sensor
51 First lens system channel
52 Second lens system channel
53 First optical axis
54 Second optical axis
56 Longitudinal axis
80 Printed circuit board

What is claimed is:

1. An optical system for an endoscope, the optical system comprising:
    a distal optical assembly;
    a proximal optical assembly; and
    at least one elongated bar-shaped fixing element;
    wherein the proximal optical assembly is fastened to the distal optical assembly by the fixing element;
    the proximal optical assembly comprises a first holder and a second holder each configured to receive an image sensor; and
    the at least one fixing element comprises a first fixing element and a second fixing element, wherein each of the first holder and the second holder has a first fixing region and a second fixing region, the first fixing element fixes the distal optical assembly to the first fixing region of the second holder and to the second fixing region of the first holder, and the second fixing element fixes the distal optical assembly to the first fixing region of the first holder and to the second fixing region of the second holder.

2. The optical system according to claim 1, wherein the first fixing element and the second fixing element are each elongated in a direction parallel to a longitudinal axis of the optical system.

3. The optical system according to claim 2, wherein the first fixing element and the second fixing element each have a cylindrical cross section, and a cylinder axis of each of the first fixing element and the second fixing element extend parallel to the longitudinal axis of the optical system.

4. The optical system according to claim 1, wherein each of the first fixing element and the second fixing element are formed integrally with the distal optical assembly.

5. The optical system according to of claim 1, wherein each of the first fixing element and the second fixing element are formed separately from and are fixed to, a mount in the distal optical assembly.

6. The optical system according to claim 5, wherein each of the first fixing element and the second fixing element are fixed to the mount in the distal optical assembly by welding.

7. The optical system according to claim 6, wherein each of the first fixing element and the second fixing element are formed from a base material and provided with a coating, wherein the coating has better solderability than the base material.

8. The optical system according to claim 5, wherein each of the first fixing element and the second fixing element are formed from a base material and the mount in the distal optical assembly is formed from a mount material, wherein the base material differs from the mount material.

9. The optical system according to claim 1, wherein each of the first fixing element and the second fixing element are fixed to the proximal optical assembly by a soldered connection.

10. The optical system according to claim 1, wherein the first holder is arranged axisymmetrically with respect to the second holder relative to a longitudinal axis of the optical system.

11. The optical system according to claim 1, further comprising a first lens system channel having a first optical axis and a second lens system channel having a second optical axis, wherein the first optical axis runs parallel to the second optical axis and to the longitudinal axis of the optical system, and the first fixing element is arranged above the first lens system channel and the second fixing element is arranged below the second lens system channel.

12. An endoscope comprising an optical system according to claim 1.

13. A method for fixing a proximal optical assembly to a distal optical assembly of an optical system for an endoscope, that the method comprising:
    fixing the distal optical assembly to a first elongated bar-shaped fixing element;
    fixing the distal optical assembly to a second elongated bar-shaped fixing element;
    fixing the first elongated bar-shaped fixing element to a first fixing region of a second holder of the proximal optical assembly and to a second fixing region of a first holder of the proximal optical assembly; and
    fixing the second elongated bar-shaped fixing element to a first fixing region of the first holder and to a second fixing region of the second holder.

14. The method according to claim 13, wherein each of the first and second elongated bar-shaped fixing elements are elongated, following fixing, in a direction parallel to a longitudinal axis of the optical system.

15. The method according to claim 13, wherein each of the first and second elongated bar-shaped fixing elements are formed integrally with the distal optical assembly.

16. The method according to claim 13, each of the first and second elongated bar-shaped fixing elements are formed separately from and are fixed to a mount in the distal optical assembly.

17. The method according to claim 16, wherein each of the first and second elongated bar-shaped fixing elements are formed from a base material and a coating, the coating having better solderability than the base material.

18. The method according to claim 13, wherein each of the first and second elongated bar-shaped fixing elements are fixed to the proximal optical assembly by a soldered connection.

\* \* \* \* \*